United States Patent [19]

Tanabe et al.

[11] 4,062,900
[45] Dec. 13, 1977

[54] PROCESS FOR PREPARING BUTANEDIOL AND/OR BUTENEDIOL

[75] Inventors: Yasuo Tanabe; Jun Toriya; Masato Sato; Ken Shiraga, all of Kurashiki, Japan

[73] Assignee: Mitsubishi Chemical Industries Limited, Tokyo, Japan

[21] Appl. No.: 705,718

[22] Filed: July 15, 1976

[30] Foreign Application Priority Data

Aug. 7, 1975 Japan .................... 50-96153

[51] Int. Cl.$^2$ .............................. C07C 29/24
[52] U.S. Cl. .................... 260/637 R; 260/643 F
[58] Field of Search .............. 260/637 R, 643 F

[56] References Cited

U.S. PATENT DOCUMENTS

| 2,868,832 | 1/1959 | Taylor et al. | 260/643 F |
|---|---|---|---|
| 3,647,892 | 3/1972 | Hoch | 260/637 R |
| 3,852,164 | 12/1974 | Chow et al. | 260/637 R |
| 3,891,511 | 6/1975 | Danneil et al. | 260/637 R |
| 3,917,720 | 11/1975 | Webb et al. | 260/637 R |

FOREIGN PATENT DOCUMENTS

| 470,663 | 1/1951 | Canada | 260/637 R |

Primary Examiner—James O. Thomas, Jr.
Assistant Examiner—G. T. Breitenstein
Attorney, Agent, or Firm—Bierman & Bierman

[57] ABSTRACT

Butanediol and/or butenediol are prepared by hydrolyzing diacetoxybutane and/or diacetoxybutene in the presence of a cation-exchange resin and recovered by fractional distillation. By the treatment of the hydrolyzed product with an anion exchange resin at any stage before the butanediol and/or butenediol are fractionated, butanediol and/or butenediol are recovered in high yield.

8 Claims, No Drawings

PROCESS FOR PREPARING BUTANEDIOL AND/OR BUTENEDIOL

BACKGROUND OF THE INVENTION

1. Field of the Invention

This invention relates to a process for preparing butanediol and/or butenediol. More particularly, this invention relates to a process for preparing butanediol and/or butenediol in high yield by hydrolyzing diacetoxybutane and/or diacetoxybutene in the presence of a cation-exchange resin and distilling the hydrolyzed product to obtain butanediol and/or butenediol.

2. Description of Prior Art

Butanediols, particularly 1,4-butanediol are attracting more and more interests in recent years because they form polyesters with terephthalic acid which are useful molding materials having excellent physical properties. Further, butanediol is also useful as a starting material for synthesizing chemicals which are commercially valuable, such as tetrahydrofuran, γ-butyrolactone or the like.

It is known that butanediol or butenediol can be prepared by hydrolyzing diacetoxybutane or diacetoxybutene. Use of a acid cation-exchange resin as the catalyst for the above hydrolysis is also known, but, when the acid cation-exchange resin is used for the hydrolysis, a part of the acidic segments of the resin is eluted in the resulting liquid. For example, if a strong acid cation-exchange resin having sulfo-groups is used, acidic substances such as $-SO_3H$ radicals are eluted in the reaction liquid. Such acidic substances, even at concentrations as low as several parts per million in the liquid, may unfavorably affect the thermostability of butanediol and butanediol to a large extent and result in the formation of cyclic ether by-products such as tetrahydrofuran, etc., reducing the recovery of butanediol and butenediol.

SUMMARY OF THE INVENTION

Accordingly, it is one object of this invention to provide an industrially advantageous process for manufacturing butanediol and/or butenediol.

It is another object of this invention to provide a process for recovering butanediol and/or butenediol in high yield from hydrolyzed reaction products of acetic acid ester thereof by distillation.

Furthermore, it is another object of this invention to provide a process for reducing the formation of by-products in the course of the distillation by removing acidic substances which elute from an acid cation-exchange resin in hydrolysis.

These and other object of the present invention have been attained by treating the hydrolyzed reaction product containing butanediol and/or butenediol with an anion-exchange resin at any stage before the butanediol and/or butenediol are fractionated.

DETAILED DESCRIPTION OF THE PREFERRED EMBODIMENTS

Diacetoxybutane and diacetoxybutene which are starting materials in the present invention are generally prepared by the oxidative acetoxylation of butadiene and acetic acid. This reaction may be carried out in various known methods. Diacetoxybutene can be prepared by reacting butadiene, acetic acid, and oxygen or an oxygen-containing gas in the presence of a palladium series catalyst by a fixed bed, fluidized bed or suspension process. The catalysts which may be used in the acetoxylation include homogeneous liquid phase catalysts comprising a palladium salt and a redox agent such as a copper salt, and solid catalysts comprising a metal such as palladium, platinum, rhodium, iridium or ruthenium or a salt thereof, optionally in combination with another metal such as copper, silver, zinc, nickel, chromium, iron, cobalt, cadmium, tin, lead, molybdenum, tungusten, antimony, tellurium, selenium, bismuth, an alkaline metal or an alkaline earth metal or a salt thereof as a co-catalyst. Among those most preferred are catalysts comprising palladium metal and at least one co-catalyst metal selected from bismuth, selenium, antimony, and tellurium on a suitable carrier.

As a starting material for the present method, there is used a mixture of diacetoxybutene isomers such as 1,4-diacetoxybutene-2, 3,4-diacetoxybutene-1, obtained from the acetoxylation product by distillation separation. As the case may be, the mixture of diacetoxybutenes can be separated into respective isomers before use as a starting material. Also, diacetoxybutenes which can be prepared by reacting 1,3- and 1,4-dichlorobutene, acetic acid, and sodium acetate in the presence of a metal salt catalyst may be used as the starting material for the present method.

The acetoxybutanes can be obtained by hydrogenating diacetoxybutenes in the presence of a palladium or nickel series catalyst. These diacetoxybutanes can be used as a starting material in any desired form whether they are in admixture of isomers or separated into respective isomers such as 1,4-, 1,2-, and 1,3-diacetoxybutanes or the like, or contain unreacted diacetoxybutenes.

At the hydrolysis step according to the present invention, diacetoxybutane and/or diacetoxybutene are reacted with water in the presence of a cation-exchange resin catalyst. The cation-exchange resin used herein may include strong acid and weak acid cation-exchange resins. But, the strong acid cation-exchange resins which consist of styrene-divinylbenzene copolymers with sulfo-groups as a functional group are preferable. Any type, for example, a gel or porous type of resins may be used, which are commercially available from Mitsubishi Chemical Industries Ltd. Tokyo, Japan, under trade names of DIAION SK 1B, SK 103, SK 106 (a gel type), PK 206, PK 216, and PK 228 (a porous type).

The hydrolysis may be carried out in any desired manner; for example, by making the reagents in contact with the ion-exchange resin in suspension or by passing the reagents through a bed packed with the ion-exchange resin. The latter process is commercially advantageous.

The hydrolysis may be carried out generally at a temperature of 30° to 120° C, preferably at a temperature of 40° to 100° C. At too low a temperature, the rate of reaction is unacceptably low; on the other hand, at too high a temperature, sub-reactions forming tetrahydrofuran, dihydrofuran and the like may often occur. Another reason for selection of this temperature range is to prevent the degradation of the cation-exchange resin and to reduce the elution from the resin to some extent.

However, it is difficult in practice to prevent the elution of acidic radicals of the resin during hydrolysis. The eluted acidic substances, particularly $-SO_3H$ radicals eluted from a strong acid cation-exchange resin cause lowering of the recovery of butanediol and/or butenediol during the fractional distillation thereof, even when they are present in trace amounts as, for example, several parts per million. So, the presence of such acidic substances during the distillation should be avoided. To this end the hydrolyzed products should be subjected to treatment with an anion-exchange resin in order to remove them, prior to the distillation, according to this invention.

As the anion-exchange resin according to this invention, strongly or weakly basic anion-exchange resins may be used.

The resin may be of the gel or porous type. Among these preferred are weakly basic anion-exchange resins, the matrix of which mainly consists of styrene-divinylbenzene copolymers and which have primary, secondary or tertiary amine groups. They are effective in suppressing subreactions and the contamination of the treated liquid by chlorine ions. Available examples of the weakly basic anion-exchange resins are DIAION WA-10 and WA-11 a gel-type, Cross linked polyacrylate matrix (the tertiary amine-form); Diaion WA-20 and WA-21, a porous-type cross linked polystyrene matrix. (the primary or secondary amine-form); and Diaion WA-30, a highly porous type crosslinked polystyrene matrix (the tertiary amine-form), all manufactured by Mitsubishi Chemical Industries Limited.

As the hydrolyzed product to be treated with an anion-exchange resin according to this invention, there can be used the effluent from the hydrolysis reaction bed of the cation-exchange resin as is; the liquid obtained by removing the cation-exchange resin from the hydrolyzed reaction medium in suspension process; the mixture obtained from the hydrolysis product from which water and acetic acid have been separated, including unreacted material such as diacetoxybutane and/or diacetoxybutene, partially esterified products such as acetoxyhydroxybutane and/or acetoxyhydroxybutene, butanediol and/or butenediol and high-boiling substances; or the partially esterified products and the unreacted material removed from the above-described mixture by distillation.

However, direct treatment of the solution obtained after the hydrolysis is most preferable in the present method.

For the treatment of the hydrolyzed solution with the anion-exchange resin, there are no critical limitations and no specific restrictions as to the method. For example, the solution may be either passed through a bed packed with the anion-exchange resin in an upward or downward direction, or contacted with the resin in suspension with stirring and then filtered. The packed bed system is generally used, while the suspension system may be used unless the solution can form a homogeneous phase.

Since substantially no reaction heat is generated during the treatment, neither cooling nor heating means is necessary. This fact, however, does not exclude their use.

The treating temperature is generally from 20° to 100° C, preferably from 50° to 80° C. Temperatures outside of this range are not suitable, because the liquid under the treatment will coagulate at temperatures below 20° C, while the function of the anion-exchange resin considerably reduces at temperatures above 100° C.

The anion-exchange resin may be employed in an amount of 0.0001 to 1 part by weight (preferably 0.001 to 0.1 part by weight) per one part by weight of the strong acid cation-exchange resin employed for the hydrolysis.

When the anion-exchange resin is used in the form of a packed bed, the hydrolyzed liquid is supplied to the packed bed generally at an SV (space velocity in a column) of 1000 to 0.1 hr$^{-1}$, preferably at an SV of 100 to 1 hr$^{-1}$.

After the treatment with the anion-exchange resin, the resulting solution is supplied to a distillation column, the bottom of which is maintained at a temperature of 150° to 220° C (preferably at a temperature of 170° to 200° C), to obtain butanediol and/or butenediol.

The distillation can be carried out batchwise or continuously. Generally, a continuous process in a distillation column is used. When butanediol and/or butenediol is distilled off from a solution thereof, it is preferable to maintain a partial pressure of oxygen in the distillation column of not more than 10 mmHg. This can prevent the production of undesired by-products to obtain more highly purified butanediol and/or butenediol.

When diols are desired in especially high purity e.g. over (99%), the partial pressure of oxygen is maintained at less than 5 mmHg, more preferably less than 1 mmHg.

To maintain oxygen, the following methods may be used;

1. the solution including the reacton products, prior to supply to the distillation system, may be degased sufficiently to decrease the amount of dissolved oxygen in said solution;

2. if vacuum distillation is used to recover the diols, the apparatus is selected from those which do not leak air and the airtightness of all joints is maintained so as to keep the partial oxygen pressure, or covers are provided over the joints and inert gas, such as nitrogen, occupies the space between the joints and the covers.

Suitably, such methods may be used singly or in combination.

As is apparent from the foregoing, the acidic substances which are eluted from the cation-exchange resin when diacetoxybutane and/or diacetoxybutene are hydrolyzed in the presence of the cation-exchange resin as the catalyst and reduce the recovery of butanediol and/or butenediol during the distillation thereof. They can be easily removed by treating the hydrolyzed liquid with the anion-exchange resin according to the invention. Therefore, the formation of by-products during the distillation is reduced to a reasonable level and the recovery of butanediol and/or butenediol is greatly improved.

Having generally described the invention, a more complete understanding can be obtained by reference to certain specific examples, which are included for purposes of illustration only and are not intended to be limiting unless otherwise specified.

EXAMPLE 1

A pyrex reactor surrounded with a jacket and having a diameter of 40 mm and a height of 400 mm was filled with 500 ml of a strong acid cation-exchange resin, DIAION SK 1B (trade mark, manufactured by Mitsubishi Chemical Industries Limited), swelled with water. Warm water was fed through the jacket to maintain the temperature of the reactor at 50° C. In front of the reactor, a pipe filled with packings of SUS-316 and having a diameter of 25 mm and a length of 300 mm was placed to form a dissolving region. The temperature of the pipe was also maintained at 50° C by means of a warm water jacket.

1,4-diacetoxybutane used as a starting material was obtained by reacting butadiene, acetic acid, and oxygen-containing gas in the presence of a palladium series catalyst to obtain 1,4-diacetoxybutene-2, and then hydrogenating 1,4-diacetoxybutene-2 in the presence of the palladium series catalyst.

A mixture of 1,4-diacetoxybutane and a previously hydrolyzed product thereof and water were fed by means of a constant rate pump at a rate of 601.5 g/hr and 398.5 g/hr., respectively, into the upper portion of the reactor maintained at normal pressure and 50° C. Under these conditions hydrolysis was carried out in the reactor.

The hydrolyzed liquid discharged from the bottom of the reactor had the following composition:

| | |
|---|---|
| tetrahydrofuran | 0.0 g/hr |
| water | 369.5 g/hr |
| acetic acid | 143.7 g/hr |
| 1,4-diacetoxybutane | 52.1 g/hr |
| 1-acetoxy-4-hydroxybutane | 223.5 g/hr |
| 1,4-butanediol | 211.2 g/hr |

The above liquid is named Sample A hereinafter.

A pyrex column surrounded with a jacket and having a diameter of 25 mm and a length of 300 mm was filled with 100 ml of a weakly basic anion-exchange resin, DIAION WA-20 (trade mark, manufactured by Mitsubishi Chemical Industries Limited). Warm water was fed through the jacket to maintain the temperature of the reactor at 50° C.

Sample A was fed to the WA-20 packed bed by means of a constant rate pump at a rate of 1,000 ml/hr. The effluent discharged from the bottom of the column was then distilled in the following manner to remove water and acetic acid and separated a butanediol fraction.

As a distillation column was used a 20-stage plate column (inner diameter 35 mm) made of pyrex which was equipped with a vacuum jacket. In the bottom of the plate column was charged about 682 g of the effluent, ie., the liquid treated with the anion-exchange resin. Fractional distillation of water and acetic acid was carried out for 3 hours while maintaining the pressure at the top of the column at 400 mmHg by means of a vacuum pump. The temperature at the top was 85°–100° C, the temperature at the bottom was 100°–200° C, and the reflux ratio was 1.0.

The liquid had the following compositions before and after the distillation.

| | Charged amount | Recovered amount (distilled + residual |
|---|---|---|
| tetrahydrofuran | 0.0 g | 0.2 g |
| water | 251.9 g | 252.5 g |
| acetic acid | 98.0 g | 98.6 g |
| 1,4-diacetoxybutane | 35.5 g | 34.5 g |
| 1-acetoxy-4-hydroxybutane | 152.4 g | 153.1 g |
| 1,4-butanediol | 144.0 g | 139.4 g |
| Total | 681.8 g | 678.3 g |

The recovery of diacetoxybutane, hydroxyacetoxybutane and butanediol was 98.52%.

COMPARATIVE EXAMPLE 1

Distillation was carried out in a similar manner as in Example 1 except that the hydrolzed liquid was not treated with the weakly basic anion-exchange resin.

In the bottom of the plate column was charged 570 g of Sample A prepared in Example 1, while the distillation temperature, pressure, and reflux ratio were maintained to substantially the same values.

The liquid had the following compositions before and after the distillation.

| | Charged amount | Recovered amount (distilled + residual) |
|---|---|---|
| tetrahydrofuran | 0.0 g | 5.4 g |
| water | 210.6 g | 209.8 g |
| acetic acid | 81.9 g | 80.5 g |
| 1,4-diacetoxybutane | 29.7 g | 26.2 g |
| 1-acetoxy-4-hydroxybutane | 127.4 g | 125.7 g |
| 1,4-butanediol | 120.4 g | 111.2 g |
| Total | 570.0 g | 558.8 g |

The recovery of 1,4-diacetoxybutane, 1-acetoxy-4-hydroxybutane and 1,4-butanediol was 94.77%.

EXAMPLE 2

An acetoxylation reaction mixture of butadiene was hydrogenated and then hydrolyzed under substantially the same conditions as in Example 1 and thereafter subjected to distillation to remove water and acetic acid in a similar manner to that of Comparative Example 1. After the removal of water and acetic acid there was obtained a liquid having the following composition, which was then subjected to the treatment with an anion-exchange resin and batch distillation.

| | |
|---|---|
| tetrahydrofuran | 0.03 wt% |
| water | 0.16 wt% |
| acetic acid | 0.20 wt% |
| 1,2-diacetoxybutane | 0.30 wt% |
| 1-acetoxy-2-hydroxybutane | 2.09 wt% |
| 1,2-butanediol | 4.94 wt% |
| 1,4-diacetoxybutane | 24.90 wt% |
| 1-acetoxy-4-hydroxybutane | 52.28 wt% |
| 1,4-butanediol | 14.80 wt% |
| high boiling substances | 0.29 wt% |
| Total | 100.00 wt% |

A pyrex column surrounded with a jacket and having a diameter of 25 mm and a length of 300 mm was filled with 100 ml of a weakly basic anion-exchange resin, DIAION WA-20 (trade mark, manufactured by Mitsubishi Chemical Industries Limited). Warm water was fed through the jacket to maintain the temperature of the column at 50° C.

The above-described liquid was supplied to the WA-20 packed bed at a rate of 500 ml/hr by means of a constant rate pump. The effluent discharged from the bottom of the column was then subjected to the distillation under the following conditions.

As a distillation column was used a 40-stage plate column (inner diameter 35 mm) made of pyrex which was equipped with a vacuum jacket. In the bottom of the plate column was charged 298.6 g of the effluent, ie., the liquid treated with the anion-exchange resin. Fractional distillation of 1,4-diacetoxybutane, 1-acetoxy-4-hydroxybutane and 1,4-butanediol was carried out for 15 hours while maintaining the pressure at the top of the column at 200 mmHg by means of a vacuum pump. The temperature at the top was 175°-185° C, the temperature at the bottom was 195°-200° C and the reflux ratio was 1.0.

The liquid has the following compositions before and after the distillation.

|  | Charged amount | Recovered amount (distilled + residual |
|---|---|---|
| tetrahydrofuran | 0.1 g | 0.2 g |
| water | 0.6 g | 0.4 g |
| acetic acid | 0.6 g | 1.3 g |
| 1,2-diacetoxybutane | 0.9 g | 0.8 g |
| 1-acetoxy-2-hydroxybutane | 6.3 g | 6.0 g |
| 1,2-butanediol | 14.7 g | 14.4 g |
| 1,4-diacetoxybutane | 74.8 | 74.1 g |
| 1-acetoxy-4-hydroxybutane | 155.4 g | 154.0 g |
| 1,4-butanediol | 44.3 g | 44.1 g |
| high boiling substances | 0.9 g | 1.2 g |
| Total | 298.6 g | 296.5 g |

The recovery of 1,4-diacetoxybutane, 1-acetoxy-4-hydroxybutane and 1,4-butanediol was 99.16%.

COMPARATIVE EXAMPLE 2

Distillation was carried out in a similar manner as in Example 2 except that the liquid obtained by distilling off water and acetic acid was not treated with the weakly basic anion-exchange resin.

The liquid had the following compositions before and after the distillation.

|  | Charged amount | Recovered amount (distilled + residual) |
|---|---|---|
| tetrahydrofuran | 0.1 g | 13.3 g |
| water | 0.5 g | 1.2 g |
| acetic acid | 0.6 g | 1.8 g |
| 1,2-diacetoxybutane | 0.9 g | 0.9 g |
| 1-acetoxy-2-hydroxybutane | 6.3 g | 6.3 g |
| 1,2-butanediol | 14.8 g | 13.1 g |
| 1,4-diacetoxybutane | 74.6 g | 70.7 g |
| 1-acetoxy-4-hydroxybutane | 156.6 g | 153.8 g |
| 1,4-butanediol | 44.3 g | 26.7 g |
| high boiling substances | 0.9 g | 4.1 g |
| Total | 299.6 g | 291.9 g |

The recovery of 1,4-diacetoxybutane, 1-hydroxy-4-acetoxybutane and 1,4-butanediol was 91.18%.

EXAMPLE 3

Sample A was distilled in the same manner as in Example 1 to remove water and acetic acid. The resulting liquid was subjected to the distillation as in Comparative Example 2, yielding a liquid having the following composition;

| 1,4-butanediol | 96.0% |
|---|---|
| high boiling substances | 4.0% | which was then subjected to treatment with an anion-exchange resin and then batch distillation.

A pyrex tube surrounded with a jacket and having a diameter of 25 mm and a length of 300 mm was filled with 20 ml of a weakly basic anion-exchange resin, DIAION WA-20 (trade mark, manufactured by Mitsubishi Chemical Industries Limited). Warm water was fed through the jacket to maintain the temperature of the tube at 50° C. The liquid having above-described composition was supplied to the WA-20 packed bed at a rate of 100 ml/hr by means of a constant rate pump. The effluent discharged from the bottom was then subjected to the distillation under the following conditions.

As a distillation column was used a 20-stage plate column (inner diameter 35 mm) made of pyrex which is provided with a vacuum jacket. In the bottom of the plate column was charged the effluent, ie., the liquid treated with the anion-exchange resin. Fractional distillation of 1,4-butanediol and high boiling substances was carried out for 6 hours while maintaining the pressure at the top of the column at 100 mmHg by means of a vacuum pump. The temperature at the top was 170°-175° C, the temperature at the bottom was 175°-200° C and the reflux ratio was 1.5.

The liquid had the following compositions before and after the distillation.

|  | Charged amount | Recovered amount (distilled + residual) |
|---|---|---|
| tetrahydrofuran | 0.00 g | 1.5 g |
| water | 0.00 g | 0.3 g |
| 1,4-butanediol | 201.6 g | 198.9 g |
| high boiling substances | 8.4 g | 8.6 g |
| Total | 210.0 g | 209.3 g |

The recovery of 1,4-butanediol was 98.66%.

COMPARATIVE EXAMPLE 3

Distillation was carried out in a similar manner as in Example 3 except that the resulting liquid was not treated with the weak base anion-exchange resin.

The liquid had the following compositions before and after the distillation.

|  | Charged amount | Recovered amount (distilled + residual) |
|---|---|---|
| tetrahydrofuran | 0.00 g | 3.2 g |
| water | 0.00 g | 0.9 g |
| 1,4-butanediol | 188.3 g | 178.3 g |
| high boiling substances | 7.9 g | 11.9 g |
| Total | 196.2 g | 194.3 g |

The recovery of 1,4-butanediol was 94.85%

EXAMPLE 4

A hydrolyzed liquid was obtained in a similar manner as in Example 1 except that 1,4-diacetoxybutene-2 was used in lieu of 1,4-diacetoxybutane. Water and acetic acid were distilled off from the hydrolyzed liquid in a similar manner to that of Comparative Example 1 and the resulting liquid was subjected to the distillation described in Comparative Example 2, yielding a liquid having the following composition.

| 1,4-butenediol | 93.5 wt % |
|---|---|
| high boiling substances | 6.5 wt % |

The last liquid was subjected to the treatment with an anion-exchange resin and batch distillation as described in Example 3.

In this example, the pressure at the top of the plate column was maintained at 50 mmHg, the temperature at the top was 162° C and the temperature at the bottom was 165°-180° C, while the remaining conditions were the same as those of Example 3.

The liquid had the following compositions before and after the distillation.

|  | Charged amount | Recovered amount (distilled + residual) |
|---|---|---|
| 2,5-dihydrofuran | 0.0 g | 2.5 g |
| water | 0.0 g | 0.5 g |
| 1,4-butenediol | 197.4 g | 194.3 g |
| high boiling substances | 13.7 g | 15.0 g |
| Total | 211.1 g | 212.3 g |

The recovery of 1,4-butenediol was 98.43%.

COMPARATIVE EXAMPLE 4

Distillation was carried out in a similar manner to that of Example 4 except that the last liquid was not treated with the weakly basic anion-exchange resin.

The liquid had the following compositions before and after the distillation.

|  | Charged amount | Recovered amount (distilled + residual) |
|---|---|---|
| 2,5-dihydrofuran | 0.0 g | 3.7 g |
| water | 0.0 g | 1.0 g |
| 1,4-butenediol | 157.9 g | 143.8 g |
| high boiling substances | 11.0 g | 20.0 g |
| Total | 168.9 g | 168.5 g |

The recovery of 1,4-butenediol was 91.07%.

Having now fully described the invention, it will be apparent to one of ordinary skill in the art that many changes and modifications can be made thereto without departing from the spirit or scope of thereof.

Accordingly, what is claimed as new and desired to be secured by Letters Patent is:

1. In a process for preparing butanediol or butenediol by hydrolyzing diacetoxybutane or diacetoxybutene in the presence of a cation-exchange resin having at least one sulfo group as a functional group, and recovering butanediol or butenediol from the hydrolyzed product by distillation, the improvement which comprises treating the hydrolyzed product containing butanediol or butenediol with a weak anion-exchange resin which has a primary, secondary or tertiary amine groups at a temperature of 20° to 100° C at any stage before the butanediol or butenediol are fractionated.

2. A process for preparing butanediol or butenediol according to claim 1 wherein butanediol or butenediol is 1,4-butanediol or 1,4-butenediol.

3. A process for preparing butanediol or butenediol according to claim 1 wherein the weak anion-exchange resin has primary or secondary amine groups.

4. A process according to claim 1 wherein said temperature is 50° to 80° C.

5. A process for preparing butanediol or butenediol according to claim 1 wherein the anion-exchange resin is used in an amount from 0.0001 to 1 part by weight per one part by weight of the acid cation-exchange resin.

6. A process for preparing butanediol or butenediol according to claim 1 wherein the treatment is carried out by introducing the hydrolyzed product at a space velocity of 1000 to 0.1 hr$^{-1}$ to a bed of anion-exchange resin.

7. A process for preparing butanediol or butenediol according to claim 1 wherein the distillation and the fractionation are carried out in a distillation column, the bottom of which is maintained within the range 150° to 220° C.

8. A process according to claim 7 wherein the space velocity is from 100 to 1 hr. to the exponent $^{-1}$.

* * * * *